(12) United States Patent
Hattori

(10) Patent No.: US 6,957,563 B2
(45) Date of Patent: Oct. 25, 2005

(54) ABNORMALITY DETECTION DEVICE FOR AIR-FUEL RATIO SENSOR

(75) Inventor: Kazutaka Hattori, Okazaki (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 10/857,957

(22) Filed: Jun. 2, 2004

(65) Prior Publication Data

US 2004/0261498 A1 Dec. 30, 2004

(30) Foreign Application Priority Data

Jun. 4, 2003 (JP) .............................. 2003-159570

(51) Int. Cl.[7] .......................... G01N 7/00; G01N 21/00; G01N 33/496
(52) U.S. Cl. ...................... 73/1.06; 73/23.31; 73/23.32
(58) Field of Search .............................. 73/1.06, 118.1, 73/23.31, 23.32, 117.3, 117.2, 116, 119 R; 701/29, 99, 101; 340/348, 439

(56) References Cited

FOREIGN PATENT DOCUMENTS

| JP | A 64-69943 | 3/1989 |
|----|-----------|--------|
| JP | A 5-231216 | 9/1993 |
| JP | B2 6-3158 | 1/1994 |
| JP | A 11-153569 | 6/1999 |
| JP | A 2001-4580 | 1/2001 |

*Primary Examiner*—Hezron Williams
*Assistant Examiner*—Tamiko Bellamy
(74) *Attorney, Agent, or Firm*—Oliff & Berridge, PLC

(57) ABSTRACT

A novel abnormality detection device for an air-fuel ratio sensor able to more accurately detect an abnormality, provided with an air-fuel ratio sensor arranged in an exhaust passage of an internal combustion engine for detecting an air-fuel ratio based on a current generated in accordance with a concentration of oxygen in the exhaust gas along with application of voltage and an air-fuel ratio sensor activating means for activating the air-fuel ratio sensor, wherein the activity of the air-fuel ratio sensor is maintained even after the internal combustion engine is stopped and an abnormality of the air-fuel ratio sensor is detected based on an output of the air-fuel ratio sensor upon and/or after the elapse of a first predetermined time after the internal combustion engine is stopped.

9 Claims, 7 Drawing Sheets

ABNORMALITY DETECTION DEVICE FOR AIR-FUEL RATIO SENSOR

BACKGROUND OF THE INVENTION

1. Field of the Invention

The present invention relates to an abnormality detection device for an air-fuel ratio sensor.

2. Description of the Related Art

In the past, there has been known an internal combustion engine designed to determine a fuel injection amount and control an air-fuel ratio based on an output signal from an air-fuel ratio sensor provided in an exhaust system. In such an internal combustion engine, when an abnormality occurs in the air-fuel ratio sensor, suitable control of the air-fuel ratio becomes difficult and, for example, deterioration of the emission or various other problems occur. Therefore, it is necessary to accurately detect an abnormality of the air-fuel ratio sensor by some method or another.

In this regard, for example, Japanese Unexamined Patent Publication (Kokai) No. 2001-4580 describes a trouble diagnosis system for judging that trouble has occurred in an air-fuel ratio sensor, which gives a low output when the air-fuel ratio is lean and gives a high output when it is rich when the temperature is at least a predetermined activation temperature, when it is confirmed that it is in a high output state despite it being detected that the temperature of the air-fuel ratio sensor is lower than the activation temperature.

The system of the above publication, however, suffers from the problem that an abnormality can be detected only when the temperature of the air-fuel ratio sensor is less than the above activation temperature and an abnormality where the output of the air-fuel ratio sensor ends up becoming the lean side (that is, in this case, the low output side) cannot be detected. Further, it is difficult to detect an abnormality sufficiently accurately even by another abnormality detection system using an air-fuel ratio sensor proposed in the past. There is therefore a need for a novel abnormality detection system of an air-fuel ratio sensor.

SUMMARY OF THE INVENTION

An object of the present invention is to provide a novel abnormality detection device of an air-fuel ratio sensor which is able to more accurately detect an abnormality.

According to a first aspect of the present invention, there is provided an abnormality detection device for an air-fuel ratio sensor provided with an air-fuel ratio sensor arranged in an exhaust passage of an internal combustion engine for detecting an air-fuel ratio based on a current generated in accordance with a concentration of oxygen in the exhaust gas along with application of voltage and an air-fuel ratio sensor activating means for activating the air-fuel ratio sensor, wherein the activity of the air-fuel ratio sensor is maintained even after the internal combustion engine is stopped and an abnormality of the air-fuel ratio sensor is detected based on an output of the air-fuel ratio sensor upon and/or after the elapse of a first predetermined time after the internal combustion engine is stopped.

In general, the air-fuel ratio of exhaust gas in an exhaust passage of an internal combustion engine stabilizes a little while after the internal combustion engine is stopped. Further, when such an air-fuel ratio sensor is provided and it is maintained in activity, the air-fuel ratio gradually changes to the stoichiometric air-fuel ratio by the reaction at the air-fuel ratio sensor. According to the first aspect of the invention, since an abnormality of the air-fuel ratio sensor is detected based on the output of the air-fuel ratio sensor upon and/or after the first predetermined time has elapsed from the stoppage of the internal combustion engine, by suitably setting the first predetermined time, it is possible to detect an abnormality of the air-fuel ratio sensor utilizing the stable air-fuel ratio sensor output. Due to this, for example, it is possible to detect an abnormality of the air-fuel ratio sensor more accurately than the detection of an abnormality performed when the air-fuel ratio is fluctuating such as during air-fuel ratio control. Further, it is also possible to judge abnormality causes based on the output of the air-fuel ratio sensor.

Preferably, it is judged that the output of the air-fuel ratio sensor is abnormal when a magnitude of the output of the air-fuel ratio sensor when the first predetermined time has elapsed is larger than a predetermined magnitude.

When the air-fuel ratio sensor is operating normally, the output of the air-fuel ratio sensor fluctuates within a predetermined range (for example, −1.0 mA to 1.0 mA etc.) Therefore, in this case, by suitably setting the above predetermined magnitude, it is possible to detect an abnormality of the air-fuel ratio sensor. Further, simultaneously it is possible to identify the cause of the abnormality of the air-fuel ratio sensor as being an abnormality of output of the air-fuel ratio sensor.

Preferably, it is judged that the air-fuel ratio sensor has cracked when an amplitude of the output of the air-fuel ratio sensor, after the elapse of the first predetermined time, is larger than a predetermined amplitude.

It is known that, if the air-fuel ratio sensor cracks, the output of the air-fuel ratio sensor will fluctuate and the amplitude will become relatively large. Therefore, in this case, by suitably setting the predetermined amplitude, it is possible to detect an abnormality of the air-fuel ratio sensor and to identify the cause of the abnormality as being cracking of the air-fuel ratio sensor.

Preferably, judgment of cracking of the air-fuel ratio sensor is not performed when an air-fuel ratio shown by the output of the air-fuel ratio sensor when the first predetermined time has elapsed is leaner than a predetermined air-fuel ratio.

When the degree of leanness of the air-fuel ratio of the exhaust gas is high, the effect on the detected air-fuel ratio (output of air-fuel ratio sensor) due to cracking of the air-fuel ratio sensor becomes small, so the precision of the judgment of cracking of the air-fuel ratio sensor is liable to fall. In this case, when the air-fuel ratio shown by the output of the air-fuel ratio sensor when the first predetermined time has elapsed is leaner than the predetermined air-fuel ratio, it is not judged if there is cracking of the air-fuel ratio sensor, so by suitably setting the predetermined air-fuel ratio, it is possible to prevent in advance an erroneous judgment relating to cracking of the air-fuel ratio sensor.

Preferably, it is judged that there is a leak in an exhaust pipe forming the exhaust passage when the output of the air-fuel ratio sensor when a second predetermined time longer than the first predetermined has elapsed after the internal combustion engine has stopped changes to the lean side more than a predetermined change from the output of the air-fuel ratio sensor when the first predetermined time has elapsed.

If there is a leak in the exhaust pipe forming the exhaust passage, air will invade the exhaust passage, so the output of the air-fuel ratio sensor will change to the lean side. Therefore, in this case, by suitably setting the predetermined change, it is possible to detect an abnormality of the air-fuel ratio sensor and to identify the cause of the abnormality as being a leak of the exhaust pipe.

Preferably, judgment of leakage of the exhaust pipe is not performed when the air-fuel ratio shown by the output of the air-fuel ratio sensor when the first predetermined time has elapsed is leaner than a predetermined air-fuel ratio.

When the degree of leanness of the air-fuel ratio of the exhaust gas is high, the effect of a leak of the exhaust pipe on the detected air-fuel ratio (air-fuel ratio sensor output) becomes smaller, so the precision of judgment of a leak of the exhaust pipe is liable to fall. In this case, when the air-fuel ratio shown by the output of the air-fuel ratio sensor when the first predetermined time has elapsed is leaner than the predetermined air-fuel ratio, it is not judged if there is a leak of the exhaust pipe, so by suitably setting the predetermined air-fuel ratio, it is possible to prevent in advance erroneous judgment relating to a leak of the exhaust pipe.

Preferably, when the air-fuel ratio shown by the output of the air-fuel ratio sensor when the first predetermined time has elapsed is leaner than the predetermined air-fuel ratio, an abnormality of the air-fuel ratio sensor is detected based on the output of the air-fuel ratio sensor upon and/or after the elapse of a third predetermined time longer than the first predetermined time from when the internal combustion engine is stopped.

As explained above, when the degree of leanness of the air-fuel ratio of the exhaust gas is high, the precision of the judgment of an abnormality such as judgment of cracking of the air-fuel ratio sensor or judgment of a leak of the exhaust pipe is liable to fall. Therefore, to detect an abnormality of the air-fuel ratio sensor more accurately, it is preferable to detect if there is an abnormality in the state where the degree of leanness of the air-fuel ratio of the exhaust gas is low to a certain extent. Further, if the air-fuel ratio sensor is operating normally, as explained above, after the internal combustion engine stops, the air-fuel ratio of the exhaust gas should change gradually to the stoichiometric air-fuel ratio due to the reaction at the air-fuel ratio sensor. Due to this, in this case, by detecting if there is an abnormality after the degree of leanness of the air-fuel ratio of the exhaust gas becomes low to a certain extent or by changing the air-fuel ratio of the exhaust gas by the reaction at the air-fuel ratio sensor over a relatively long time and detecting if there is an abnormality in the air-fuel ratio sensor based on this change, it becomes possible to detect an abnormality in an air-fuel ratio sensor more accurately.

According to a second aspect of the present invention, there is provided an abnormality detection device for an air-fuel ratio sensor provided with an air-fuel ratio sensor arranged in an exhaust passage of an internal combustion engine for detecting an air-fuel ratio based on a current generated in accordance with a concentration of oxygen in the exhaust gas along with application of voltage and an air-fuel ratio sensor activating means for activating the air-fuel ratio sensor, wherein the activity of the air-fuel ratio sensor is maintained even after the internal combustion engine is stopped and an abnormality of the air-fuel ratio sensor is detected based on a speed of change of output of the air-fuel ratio sensor after the elapse of a first predetermined time after the internal combustion engine is stopped.

As explained above, when the above air-fuel ratio sensor is provided and maintained in activity even after the internal combustion engine is stopped, the air-fuel ratio of the exhaust gas in the exhaust passage of the internal combustion engine stabilizes a little while after the internal combustion engine is stopped, then gradually changes to the stoichiometric air-fuel ratio due to the reaction at the air-fuel ratio sensor. The change in the air-fuel ratio occurs due to the reaction at the air-fuel ratio sensor, so if an abnormality occurs in the air-fuel ratio sensor, there is an effect on the speed of change of the output of the air-fuel ratio sensor. For example, when the speed of the reaction falls due to the deterioration of the air-fuel ratio sensor, the speed of change of the output of the air-fuel ratio sensor becomes smaller. Further, the degree of leakage of the exhaust pipe etc. also have an effect on the speed of change of the output of the air-fuel ratio sensor. Therefore, in this case as well it is possible to accurately detect an abnormality of the air-fuel ratio sensor and possible to estimate the degree of deterioration of the air-fuel ratio sensor and the degree of leakage of the exhaust pipe.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Figure 1:
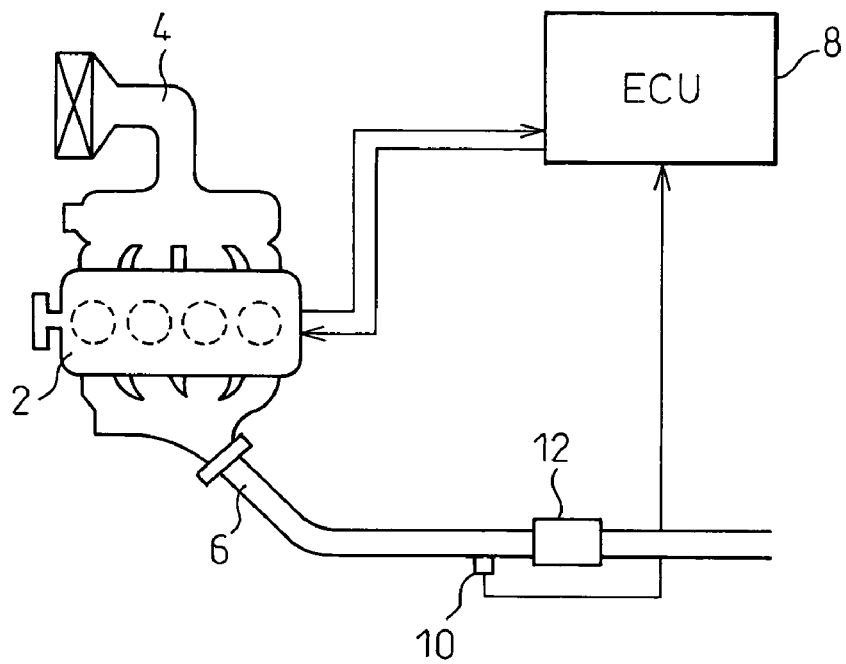
FIG. 1 is an explanatory view of the overall configuration of an internal combustion engine using the abnormality detection device for an air-fuel ratio sensor of an embodiment of the present invention.

Preferred embodiments of the present invention will be described in detail below while referring to the attached figures. Note that in the figures, the same or similar components are assigned common reference numerals.

FIG. 1 is an explanatory view of the overall configuration of an internal combustion engine using the abnormality detection device for an air-fuel ratio sensor of an embodiment of the present invention. In FIG. 1, 2 indicates an engine body, 4 an intake pipe forming an intake passage, and 6 an exhaust pipe forming an exhaust passage. As shown in FIG. 1, the exhaust passage formed by the exhaust pipe 6 is provided with an exhaust gas purification device 12 for purifying the exhaust gas. Further, the exhaust gas purification device 12 is provided upstream of it with an air-fuel ratio sensor 10 for detecting the air-fuel ratio of the exhaust gas. This air-fuel ratio sensor 10 will be explained in detail later. Note that in this example, the air-fuel ratio sensor 10 is provided upstream of the exhaust gas purification device 12, but the present invention is not limited to this. The air-fuel ratio sensor 10 may also be provided downstream of the exhaust gas purification device 12.

An electronic control unit (ECU) 8 is comprised of a known-type digital computer including a central processing unit (CPU), a random access memory (RAM), a read only memory (ROM), and input/output ports connected to each other by a bidirectional bus. It transmits and receives signals with various sensors and operating devices provided for controlling the internal combustion engine so as to control the internal combustion engine. In particular, in the present embodiment, the air-fuel ratio sensor 10 is connected to the ECU 8. The fuel injection amount etc. are determined and the air-fuel ratio controlled based on the output signal from the air-fuel ratio sensor 10 (that is, the detected air-fuel ratio).

Figure 2:
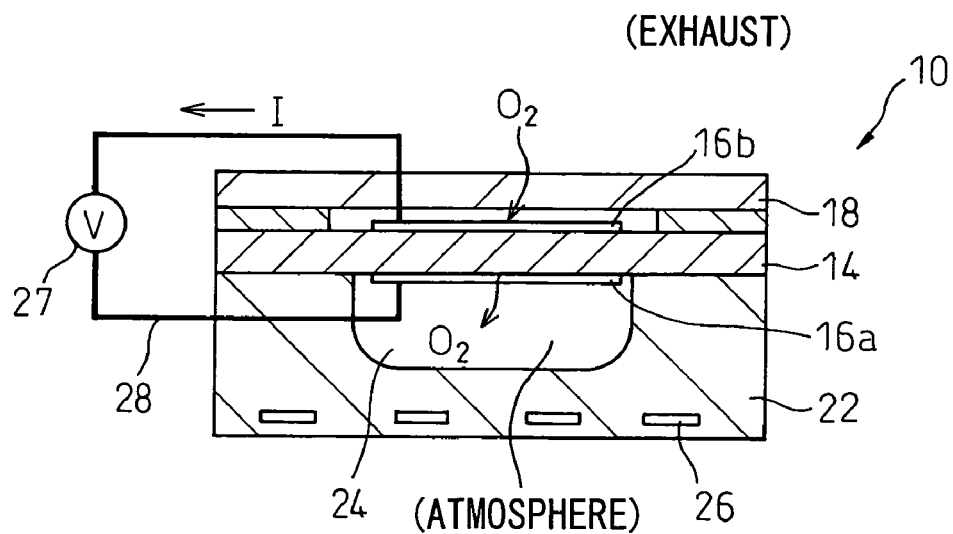
FIG. 2 is an explanatory view of the configuration of an air-fuel ratio sensor in cross-section and shows the case where the air-fuel ratio of the exhaust gas is lean.

Next, the air-fuel ratio sensor 10 will be explained in detail with reference to FIG. 2. FIG. 2 is an explanatory view of the configuration of the air-fuel ratio sensor 10 in cross-section. As shown in FIG. 2, the air-fuel ratio sensor 10 is comprised of a sintered body (for example, a zirconia or other sintered body) 14, electrodes (for example, platinum electrodes) 16a, 16b deposited on the two sides by melt spraying, a diffusion resistance layer 18, a support 22, and a heater 26 provided in the support 22. The heater 26 is for raising the temperature of the air-fuel ratio sensor 10 to at least a predetermined activation temperature where the air-fuel ratio can be detected (i.e. the heater 26 forms an air-fuel ratio sensor activating means).

Further, as shown in FIG. 2, the support 22 and the sintered body 14 define an internal space 24. This internal space 24 is communicated with the atmosphere. Further, due to this, one (16a) of the electrodes deposited on the sintered body 14 is made to contact the atmosphere (hereinafter the electrode 16a being referred to as the "atmosphere side electrode 16a"). On the other hand, the exhaust gas in the surroundings can pass through the diffusion resistance layer 18 arranged so as to cover the other electrode 16b and reach the electrode 16b. That is, the electrode 16b is made to contact the exhaust gas (hereinafter the electrode 16b being referred to as the "exhaust side electrode 16b"). Further, in this air-fuel ratio sensor 10, a circuit 28 having a power source 27 is formed, and voltage is applied at the two electrodes 16a, 16b so that the atmosphere side electrode 16a becomes a plus electrode and the exhaust side electrode 16b becomes a minus electrode.

In an air-fuel ratio sensor 10 of such a configuration, due to the principle explained below, it is possible to detect the air-fuel ratio of the exhaust gas based on the current produced in accordance with the concentration of oxygen in the exhaust gas along with the application of voltage, that is, the current flowing through the circuit 28 (output current).

That is, when the air-fuel ratio of the exhaust gas is lean, the excess oxygen ($O_2$) in the exhaust gas will pick up electrons and become ionized on the exhaust side electrode 16 and will move through the sintered body 14 to the atmosphere side electrode 16a. Further, when reaching the atmosphere side electrode 16a, the electrons will be disassociated there and oxygen returned to, so the oxygen will be released to the internal space 24. That is, when the air-fuel ratio of the exhaust gas is lean, oxygen is sucked out from the exhaust side to the atmosphere side (internal space 24) (FIG. 2). Further, along with this, movement of electrons as explained above will occur. As a result, output current I of the direction shown in FIG. 2 will be produced. Further, the magnitude of the output current I in the direction becomes greater the higher the degree of leanness of the air-fuel ratio of the exhaust gas.

Figure 3:
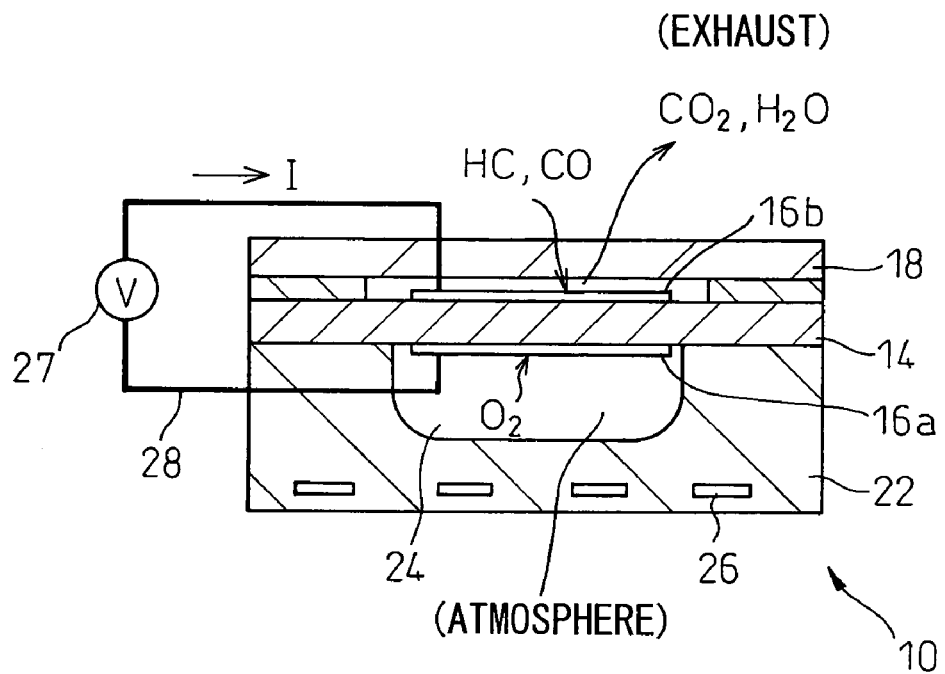
FIG. 3 is a view similar to FIG. 2 but shows the case where the air-fuel ratio of the exhaust gas is rich.

On the other hand, when the air-fuel ratio of the exhaust gas is rich, conversely, the oxygen of the atmosphere side (internal space 24) is sucked into the exhaust side and the excess hydrocarbons (HC) and carbon monoxide (CO) are reacted with (FIG. 3). At this time, the movement of electrons becomes reverse from the case where the air-fuel ratio of the exhaust gas is lean (FIG. 2), so the direction of the output current I produced becomes reverse from that of the case of FIG. 2. Further, the magnitude of the output current I of this direction becomes larger the higher the degree of richness of the air-fuel ratio of the exhaust gas.

As explained above, the value of the output current I changes according to the air-fuel ratio of the exhaust gas, so if finding in advance the relationship between the value of the output current I and the exhaust gas air-fuel ratio, it is possible to find the value of the output current I so as to find the air-fuel ratio of the exhaust gas. Further, from the above explanation, it will be learned that if the air-fuel ratio sensor 10 operates normally, regardless of whether the air-fuel ratio of the exhaust gas when the internal combustion engine is stopped is rich or lean, the air-fuel ratio gradually changes to the stoichiometric air-fuel ratio by the reaction at the air-fuel ratio sensor 10. Further, when the air-fuel ratio becomes the stoichiometric air-fuel ratio, it is considered that the output current I becomes zero.

Figure 4:
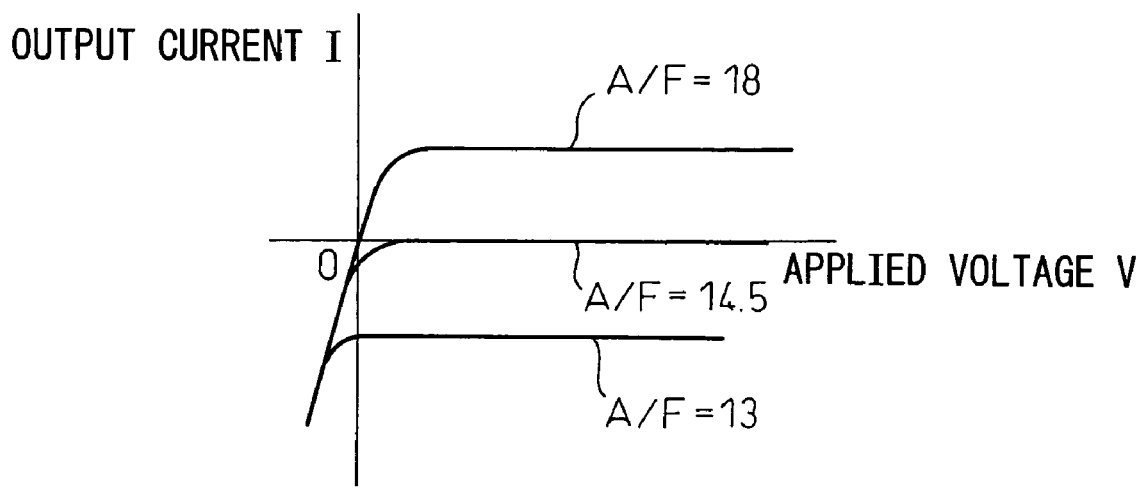
FIG. 4 is a view of the characteristic of an air-fuel ratio sensor.

Note that in the following explanation, the direction of the output current I arising when the air-fuel ratio of the exhaust gas is lean is designated as "plus", while the direction of the output current I arising when the air-fuel ratio of the exhaust gas is rich is designated as "minus". That is, FIG. 4 is a view of the characteristic of the air-fuel ratio sensor 10 wherein the abscissa indicates the applied voltage V and the ordinate the output current I. As shown in the figure, the larger the exhaust gas air-fuel ratio (A/F), the larger the value of the output current I. Further, from this figure, it can be confirmed that when the air-fuel ratio (A/F) of the exhaust gas is substantially the stoichiometric air-fuel ratio, the value of the output current I becomes substantially zero.

However, in the internal combustion engine shown in FIG. 1, as explained above, the air-fuel ratio is controlled by the ECU 8 based on the output signal (output current) from the air-fuel ratio sensor 10. Therefore, when an abnormality occurs in the air-fuel ratio sensor 10, it becomes difficult to suitably control the air-fuel ratio and for example trouble such as deterioration of the emission will occur. Accordingly, in the internal combustion engine shown in FIG. 1, by performing the control explained below, it becomes possible to accurately detect an abnormality of the air-fuel ratio sensor 10.

Figure 5:
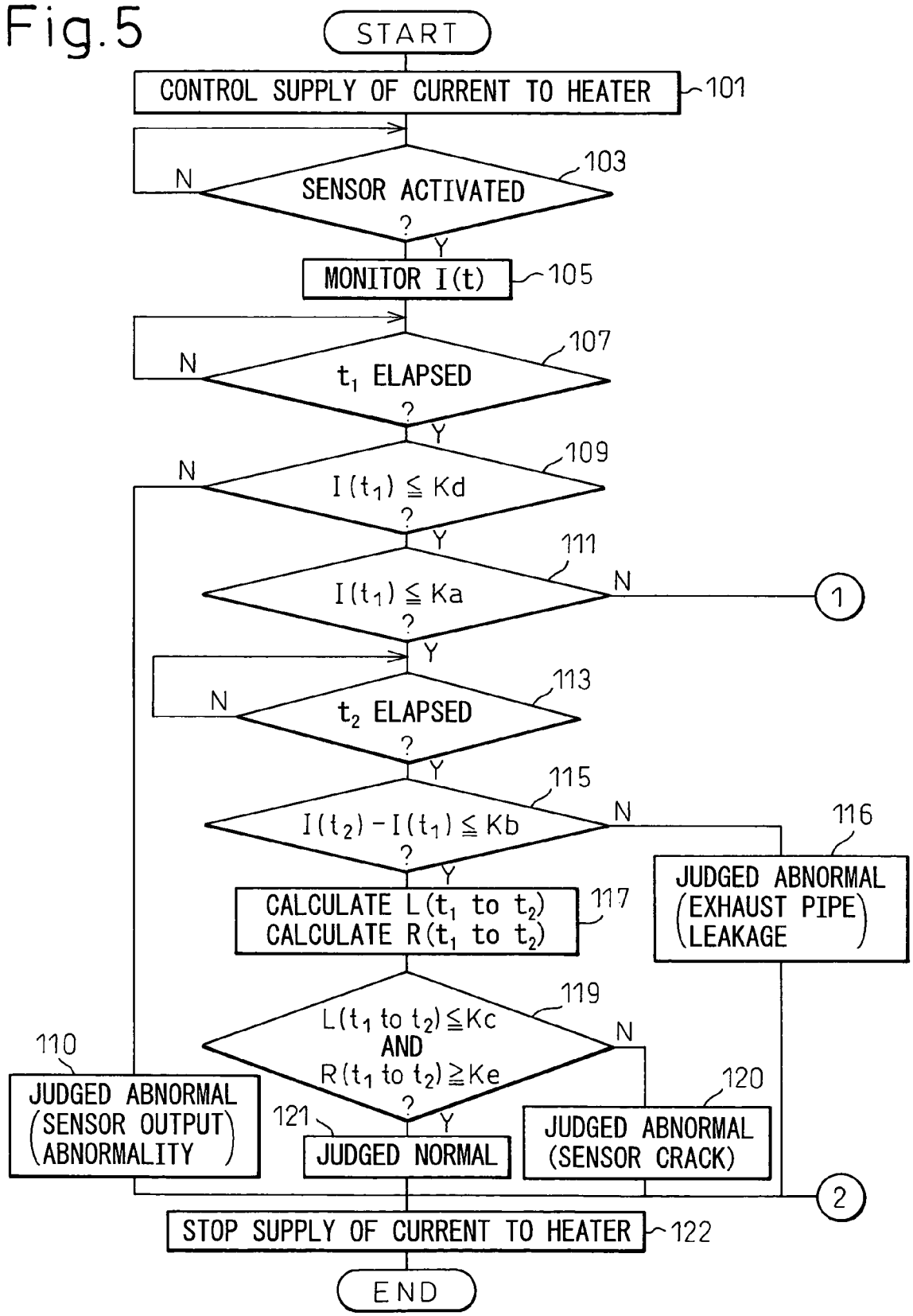
FIG. 5 is a flow chart of part of a control routine for control performed for detecting an abnormality of an air-fuel ratio sensor in the internal combustion engine shown in FIG. 1.
Figure 6:
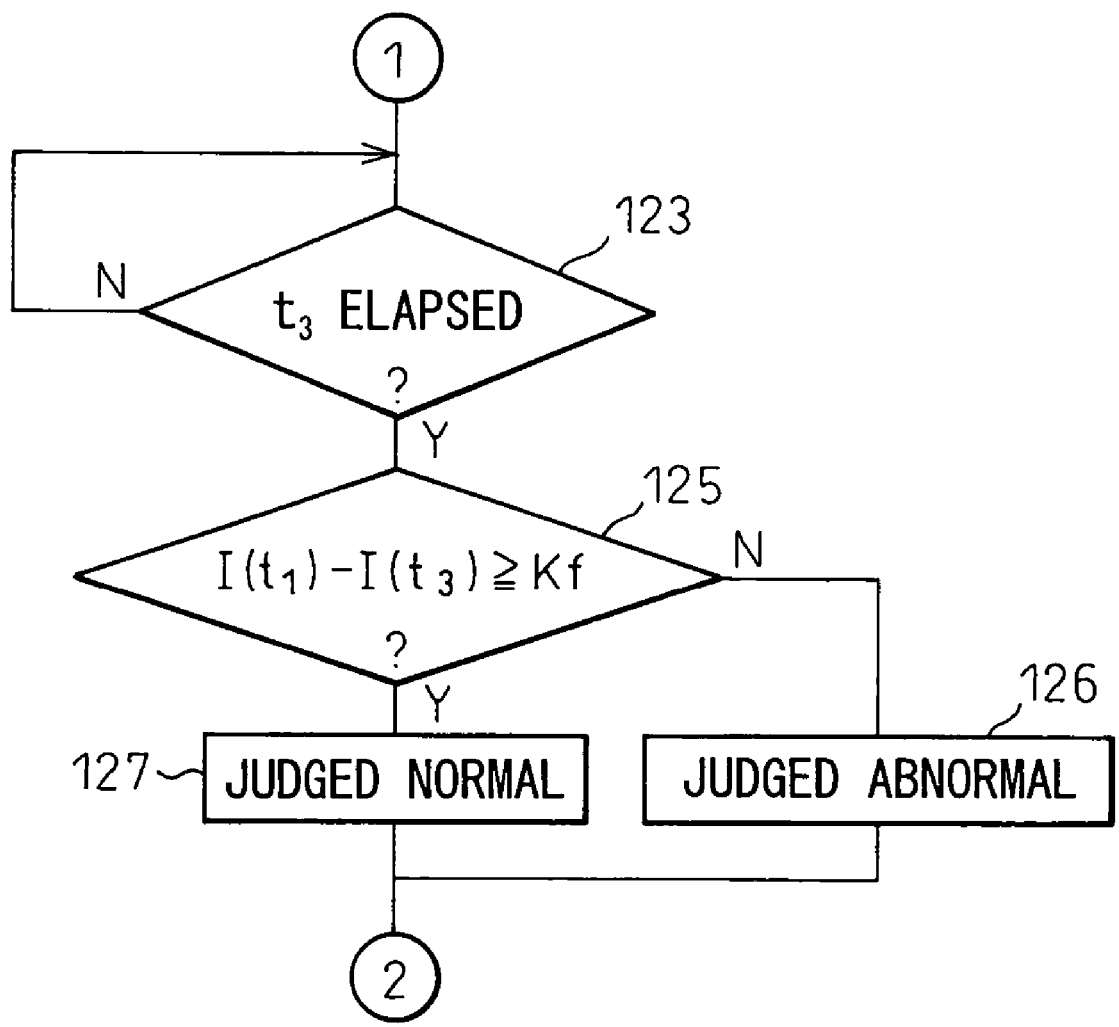
FIG. 6 is a flow chart of part of a control routine for control performed for detecting an abnormality of an air-fuel ratio sensor in the internal combustion engine shown in FIG. 1.
Figure 7:
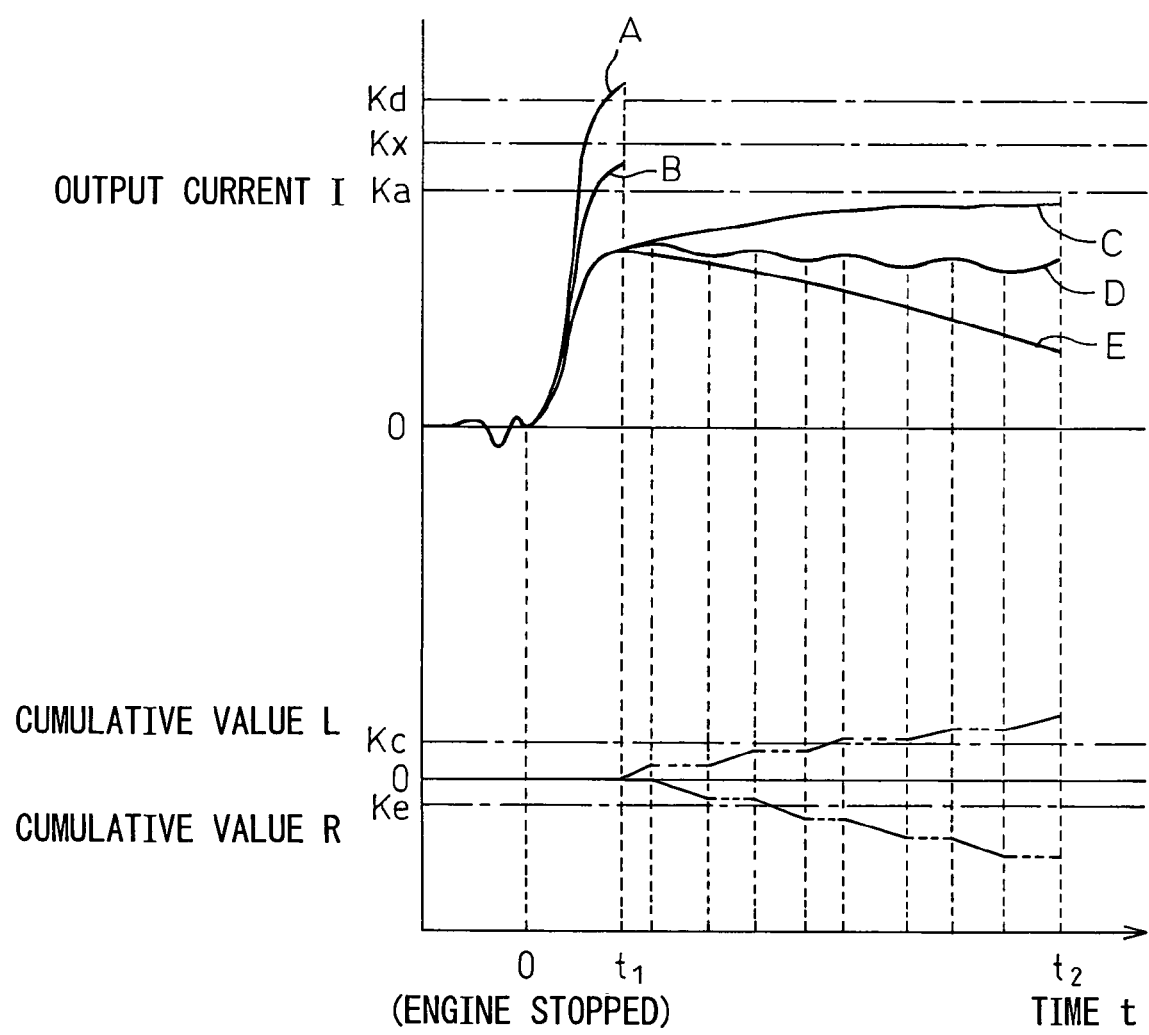
FIG. 7 is a view for explaining abnormality detection control by a control routine part shown mainly in FIG. 5 and shows a change along with time of the output current of the air-fuel ratio sensor, etc. after the internal combustion engine is stopped.
Figure 8:
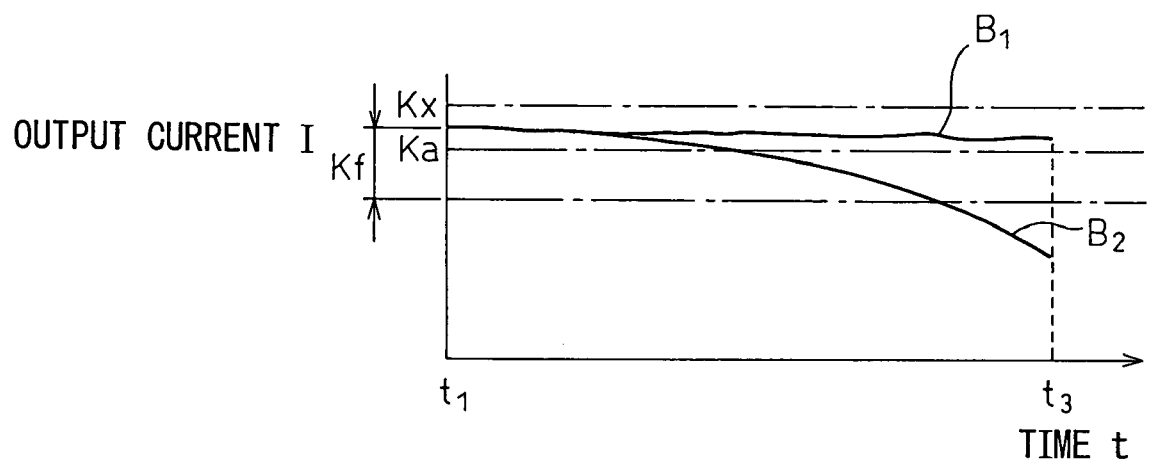
FIG. 8 is a view for explaining abnormality detection control by the control routine part shown mainly in FIG. 6 and shows a change along with time of the output current of the air-fuel ratio sensor upon and after the elapse of a first predetermined time t1 after the internal combustion engine is stopped.

FIG. 5 and FIG. 6 are flow charts of the control routine for control performed for detecting an abnormality of the air-fuel ratio sensor 10 etc. in an internal combustion engine shown in FIG. 1. Further, FIG. 7 and FIG. 8 is a view for explaining this abnormality detection control and show the change along with time of the output current I of the air-fuel ratio sensor 10, etc. after the internal combustion engine is stopped.

The control routine shown in FIG. 5 (and FIG. 6) is started by the internal combustion engine being stopped (that is, for example, by the ignition switch being turned off, the rotation of the crankshaft being stopped, etc.). When this control routine starts, first, at step 101, control is performed for supplying current to the heater 26. This current supplying control is for maintaining the temperature of the air-fuel ratio sensor 10 at least at the predetermined activation temperature so as to maintain the activity of the air-fuel ratio sensor 10 even after the internal combustion engine is stopped. Usually, the heater 26 is supplied with current before the internal combustion engine is stopped, so here control for continuing the supply of current to the heater 26 is usually performed. When the heater 26 is not supplied with current before the internal combustion engine stops, control is performed for starting the supply of current.

After step 101, at step 103, it is judged if the air-fuel ratio sensor 10 is activated or not. Here, for example, it is judged that it is activated if the temperature of the air-fuel ratio sensor 10 is a predetermined activation temperature or more, while it is judged that it is not activated if the temperature is less than the predetermined activation temperature. When it is judged at step 103 that the air-fuel ratio sensor 10 is activated, the routine proceeds to step 105. When it is judged at step 103 that the air-fuel ratio sensor 10 is still not activated, the judgment at step 103 is repeated. At the point of time when it is judged that the air-fuel ratio sensor 10 has been activated (for example, at the point of time when the temperature of the air-fuel ratio sensor 10 becomes the predetermined activation temperature or more), the routine proceeds to step 105.

When the routine proceeds to step 105, the monitoring of the output current I(t) of the air-fuel ratio sensor 10 is started (here, "t" shows the elapsed time after the internal combustion engine stops). Next, at step 107, it is judged if the elapsed time t after the internal combustion engine stops has reached a first predetermined time t1. At the point of time that the elapsed time t reaches the first predetermined time t1, the routine proceeds to step 109.

Here, the first predetermined time t1 is the waiting time until the air-fuel ratio of the exhaust gas in the exhaust passage stabilizes after the internal combustion engine is stopped and is the waiting time for the abnormality detection performed from step 109 on to be accurately performed. That is, it is learned that the air-fuel ratio of the exhaust gas in the exhaust passage of the internal combustion engine stabilizes a little while after the internal combustion engine is stopped. Further, when considering the fact that an abnormality is detected from the output current of the air-fuel ratio sensor 10, detection of an abnormality in the state where the air-fuel ratio of the exhaust gas in the exhaust passage is stable enables more accurate abnormality detection. Due to this, by performing the abnormality detection from step 109 after the elapse of the suitably set first predetermined time t1 after the engine stops, more accurate abnormality detection becomes possible. Note that the first predetermined time t1 is found by experiment etc., in advance, based on the above description.

At the next step 109, the output current I (t1) at the time when the elapsed time after the engine is stopped is t1 is found and it is judged if that value is a predetermined value Kd or less. Here, the "predetermined value Kd" is a reference value for judging if there is an abnormality in the sensor output. That is, when the air-fuel ratio sensor 10 is operating normally, the output current I of the air-fuel ratio sensor 10 fluctuates within a predetermined range. Therefore, if finding this range and determining a reference value in accordance with this in advance, it is possible to detect an abnormality in the sensor output based on this. The predetermined value Kd is a high current side (plus side) reference value for judging that the sensor output is abnormal. In the present embodiment, it is made a value slightly larger than the value Kx corresponding to the output current I at the time of measuring the atmosphere by the air-fuel ratio sensor 10. Note that it is also possible to set a low current side (minus side) reference value Kd' for judging if the sensor output is abnormal along with the predetermined value Kd and to detect any abnormality of the low current side (minus side) sensor output. Further, if comparing the magnitude of the output current I (t1) at the time of elapse of the first predetermined time t1 and the reference value |Kd| defined by the magnitude at step 109, it becomes possible to detect an abnormality of the sensor output at both the high current side (plus side) and low current side (minus side).

When it is judged at step 109 that the above output current I (t1) is the above predetermined value Kd or less, the routine proceeds to step 111. On the other hand, when it is judged that the above output current I (t1) is larger than the above predetermined value Kd, the routine proceeds to step 110, where it is judged that there is an abnormality (that is, it is judged there is an abnormality in the sensor output). Further, in this case, after step 110, the routine proceeds to step 122, where the current to the heater 26 is stopped and the control routine is ended. The change along with the elapse of time of the output current I in the case where the routine proceeds to step 110 (case of abnormality of sensor output) is for example shown by the curve A of FIG. 7.

At step 111, it is judged if the output current I (t1) when the elapsed time after the engine stops is t1 is the predetermined value Ka or less. Here, the "predetermined value Ka" is a reference value for judging if judgment of an abnormality performed from step 113 on (that is, judgment of exhaust pipe leakage and judgment of sensor cracking) is possible. That is, in the later explained judgment of exhaust pipe leakage and judgment of sensor cracking, the effect of a leak of the exhaust pipe 6 or cracking of the sensor 10 on the output current I (that is, the detected air-fuel ratio) is detected for judgment, but the effect due to this leak or cracking ends up becoming small when the degree of leanness of the exhaust gas air-fuel ratio is high. Therefore, to prevent erroneous judgment, when the degree of leanness of the exhaust gas air-fuel ratio is high (that is, when it is leaner than the predetermined air-fuel ratio used as a reference), it is preferable that judgment of exhaust gas leakage or judgment of sensor cracking not be performed. The judgment at step 111 is performed along with this gist. The above predetermined value Ka is the value of the output current I corresponding to the predetermined air-fuel ratio preset as the reference for this.

Therefore, when it is judged at step 110 that the above output current I (t1) is the above predetermined value Ka or less, it is deemed that the judgment of exhaust pipe leakage and judgment of sensor cracking can be performed and the routine proceeds to step 113. On the other hand, when it is judged that the above output current I (t1) is larger than the above predetermined value Ka, it is deemed that the judgment of exhaust pipe leakage or judgment of sensor cracking should not be performed from the air-fuel ratio, the routine proceeds to step 123 of FIG. 6, and a separate abnormality judgment process (explained later) is performed. Note that the change along with the elapse of time of the output current I when the routine proceeds to step 123 is shown for example by the curve B of FIG. 7.

At step 113, it is judged of the elapsed time t after the internal combustion engine stops has reached a second predetermined time t2. At the point of time when the elapsed time t reaches the second predetermined time t2, the routine proceeds to step 115. Here, the second predetermined time t2, only naturally, is a time longer than the above first predetermined time t1. Further, at the next step 115, the difference (I(t2)−I(t1)) between the output current I(t2) when the second predetermined time t2 elapses from when the engine is stopped and the output current (t1) when the first predetermined time t1 elapses from when the engine is stopped is found and it is judged if this value is a predetermined change Kb or less.

The judgment at step 115 judges if there is a leak in the exhaust pipe 6 forming the exhaust passage. That is, as explained above, when the air-fuel ratio sensor 10 is normally operating, the air-fuel ratio of the exhaust gas in the exhaust passage gradually changes to the stoichiometric air-fuel ratio due to the reaction at the air-fuel ratio sensor 10. However, if it is deemed that the exhaust pipe 6 is cracked and there is leakage, the air in the atmosphere invades the exhaust pipe 6, so the air-fuel ratio of the exhaust gas changes to the lean side. Therefore, if suitably setting the change of the air-fuel ratio serving as the reference in advance and finding the change Kb of the output current I corresponding to this, it can be judged that there is a leak in the exhaust pipe 6 when the output current I(t2) changes from the output current I(t1) to the lean side by more than the predetermined change Kb.

Note that when the air-fuel ratio of the exhaust gas when the first predetermined time has elapsed is rich, the air-fuel ratio of the exhaust gas changes to the lean side even by the reaction at the air-fuel ratio sensor 10, so this point has to be considered when determining the predetermined change Kb. That is, for example, it is possible to set different predetermined changes Kb1 and Kb2 for when the air-fuel ratio of the exhaust gas at the time the first predetermined time elapses is rich and when it is lean.

When it is judged at step 115 that the difference between the output current I(t2) and the output current I(t1) is larger than the predetermined change Kb, the routine proceeds to step 116, where a judgment is made by abnormalities (that is, judgment of leakage of exhaust pipe). Further, in this case, after step 116, the routine proceeds to step 122, where the current supplied to the heater 26 is stopped and this control routine is ended. The change along with the elapse of time of the output current I when the routine proceeds to this step 116 (when the exhaust pipe is leaking) is for example shown by the curve C of FIG. 7. On the other hand, when it is judged at step 115 that the difference between the output current I(t2) and the output current I(t1) is the predetermined change Kb or less, it is deemed that the exhaust pipe is not leaking and the routine proceeds to step 117.

At step 117, the cumulative value L (t1 to t2) of the rising parts of the output current I from the predetermined time t1 to t2 and the cumulative value R (t1 to t2) of the falling parts are found. The "rising part cumulative value L (t1 to t2)" is the cumulative value of the changes of rising parts in the change along with elapsed time of the output current I from the predetermined time t1 to t2. Therefore, L(t1 to t2) becomes a value of at least zero. On the other hand, the "falling part cumulative value R (t1 to t2)" is the cumulative value of the changes of falling parts in the change along with elapsed time of the output current I from the predetermined time t1 to t2 and becomes a value of zero or less.

At the next step 119, the cumulative value L(t1 to t2) and the cumulative value R(t1 to t2) found at step 117 are compared with the corresponding predetermined values Kc and Ke. More specifically, it is judged if L(t1 to t2)≦Kc and R(t1 to t2)≧Ke. Further, the judgment at step 119 is whether the air-fuel ratio sensor 10 has cracked.

That is, it is learned that if the air-fuel ratio sensor 10 has cracked, the current value I pulsates relatively largely. Further, the greater the degree of pulsation of the output current I, that is, the magnitude of the amplitude, the greater the cumulative value L(t1 to t2) in value and the smaller the cumulative value R(t1 to t2) in value. That is, the cumulative value L(t1 to t2) and the cumulative value R(t1 to t2) can be said to express the degree of pulsation of the output current I, that is, the magnitude of the amplitude. Due to this, if suitably setting the predetermined values Kc and Ke serving as the reference, it is possible to judge cracking of the air-fuel ratio sensor 10 by the judgment at step 119.

Figure 9:
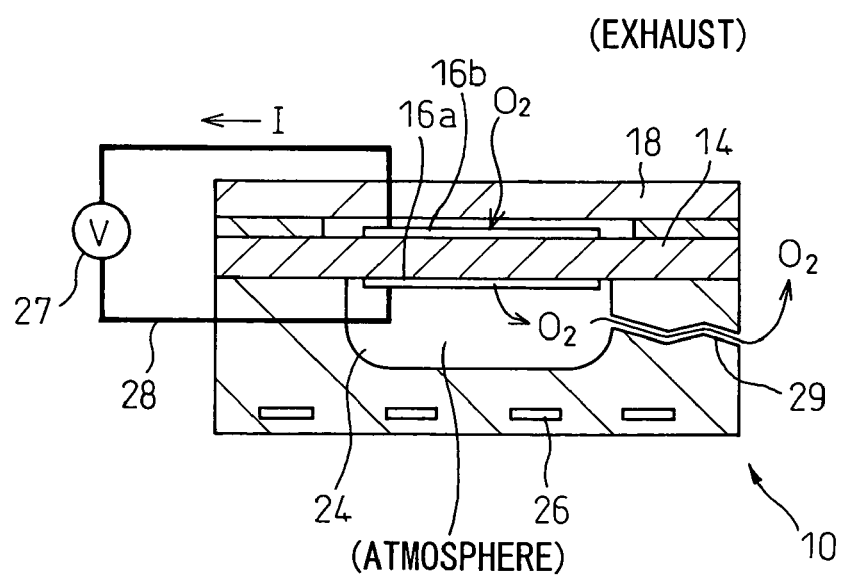
FIG. 9 is a view similar to FIG. 2 and shows the case where a crack occurs in an air-fuel ratio sensor.

Note that, as is clear from the above explanation, the predetermined value Kc is a positive value, while the predetermined value Ke is a negative value. These are set in advance by experiments etc. along with the above gist. Further, regarding the fact that the output current I pulsates when the air-fuel ratio sensor 10 is cracked, taking as an example the case where the air-fuel ratio of the exhaust gas is lean, this is believed to be due to the relationship between the pumping out action of the oxygen from the exhaust side to the atmosphere side (internal space 24) due to the air-fuel ratio sensor 10 and the leakage of the oxygen from a crack 29 in the air-fuel ratio sensor 10 (FIG. 9).

When it is judged at step 119 that L(t1 to t2)≦Kc and R(t1 to t2)≧Ke do not stand, the routine proceeds to step 120, where it is judged that there is an abnormality (that is, it is judged the sensor has cracked). Further, in this case, after step 120, the routine proceeds to step 122, where the supply of current to the heater 26 is stopped and the control routine ends. The change with the elapse of time of the output current I when proceeding to step 120 (case of cracking of sensor) is shown for example by the curve D of FIG. 7. Further, the relationship between the cumulative values L(t1 to t2) and R(t1 to t2) and the predetermined values Kc and Ke in this case is shown in the figure at the bottom of FIG. 7.

On the other hand, when it is judged at step 119 that L(t1 to t2)≦Kc and R(t1 to t2)≧Ke, the routine proceeds to step 121, where it is judged the state is normal. In this case as well, next, the routine proceeds to step 122, where the supply of current to the heater 26 is stopped and the control routine ends. The change with the elapse of time of the output current I when proceeding to step 121 (when judged normal) is for example shown by the curve E of FIG. 7.

Next, the case where it is judged that the output current I(t1) is larger than the predetermined value Ka at step 111 will be explained. As explained above, in this case, it is deemed from the air-fuel ratio that a judgment of leakage of the exhaust pipe or judgment of cracking of the sensor should not be performed and the routine proceeds to step 123 of FIG. 6, whereby another abnormality judgment process is performed.

First, at step 123, it is judged if the elapsed time t after the internal combustion engine stops has reached a third predetermined time t3. At the point of time when the elapsed time t has reached the third predetermined time t3, the routine proceeds to step 125. Here, the third predetermined time t3 is a time considerably longer than the first predetermined time t1, for example, may be about 2 or 3 hours.

Further, at the next step 125, the difference (I(t1)−I(t3)) between the output current I(t1) at the time when the first predetermined time ti elapses from when the engine stops and the output current I(t3) at the time when the third predetermined time t3 elapses from when the engine stops is found and it is judged if this value is a predetermined change Kf or more.

The judgment at step 125 is judgment of the presence of an abnormality including leakage of the exhaust pipe 6 or cracking of the air-fuel ratio sensor 10. That is, as explained above, when the air-fuel ratio sensor 10 is operating normally, the air-fuel ratio of the exhaust gas in the exhaust passage changes gradually to the stoichiometric air-fuel ratio due to the reaction at the air-fuel ratio sensor 10. However, if there is an abnormality such as cracking of the air-fuel ratio sensor 10, the speed of change of the air-fuel ratio of the exhaust gas toward the stoichiometric air-fuel ratio becomes slower. Therefore, if suitably setting the change of the air-fuel ratio serving as the reference in advance and finding the change Kf of the output current I corresponding to this, it is possible to judge the presence of an abnormality by comparing the difference between the output current I(t1) at the time of the elapse of the first predetermined time t1 and the output current I(t3) at the time of the elapse of the third predetermined time t3 with the change Kf.

When it is judged at step 125 that the difference between the output current I(t1) and the output current I(t3) is smaller than the predetermined change Kf, the routine proceeds to step 126, where it is judged there is an abnormality (in this case, it is not yet judged if the abnormality is leakage of the exhaust pipe or cracking of the sensor). In this case, after step 126, the routine proceeds to step 122, where the supply of current to the heater 26 is stopped and the control routine is ended. The change along with the elapse of time of the output current I in the case when proceeding to this step 126 (case where it is judged there is an abnormality) is shown by the curve B1 of FIG. 8 for example. On the other hand, when it is judged at step 125 that the difference between the output current I(t1) and the output current I(t3) is larger than the predetermined change Kf, the routine proceeds to step 127, where it is judged that the state is normal. In this case as well, next, the routine proceeds to step 122, where the supply of current to the heater 26 is stopped and the control routine is ended. The change along with the elapse of time of the output current I in the case when proceeding to this step 127 (case where it is judged that the state is normal) is shown by the curve B2 of FIG. 8 for example.

As explained above, according to the abnormality detection device for an air-fuel ratio sensor of the above embodiment, it is possible to more accurately detect an abnormality of the air-fuel ratio sensor 10. Further, it is also possible to judge the cause of the abnormality.

Note that it is possible to judge leakage of the exhaust pipe at step 115 in the above control routine by, instead of the above method, for example finding the above-mentioned rising part cumulative value L (t1 to t2) and comparing this value with a preset reference value. Further, for the judgment of cracking of the sensor at step 117 and step 119, what is actually performed at these steps is judgment of the extent of pulsation of the output current I, that is, the magnitude of the amplitude, so it is possible to judge cracking of the sensor even by judging the extent of the pulsation of the output current I, that is, the magnitude of the amplitude by another method. Therefore, such other method may be used to judge cracking of the sensor.

Figure 10:
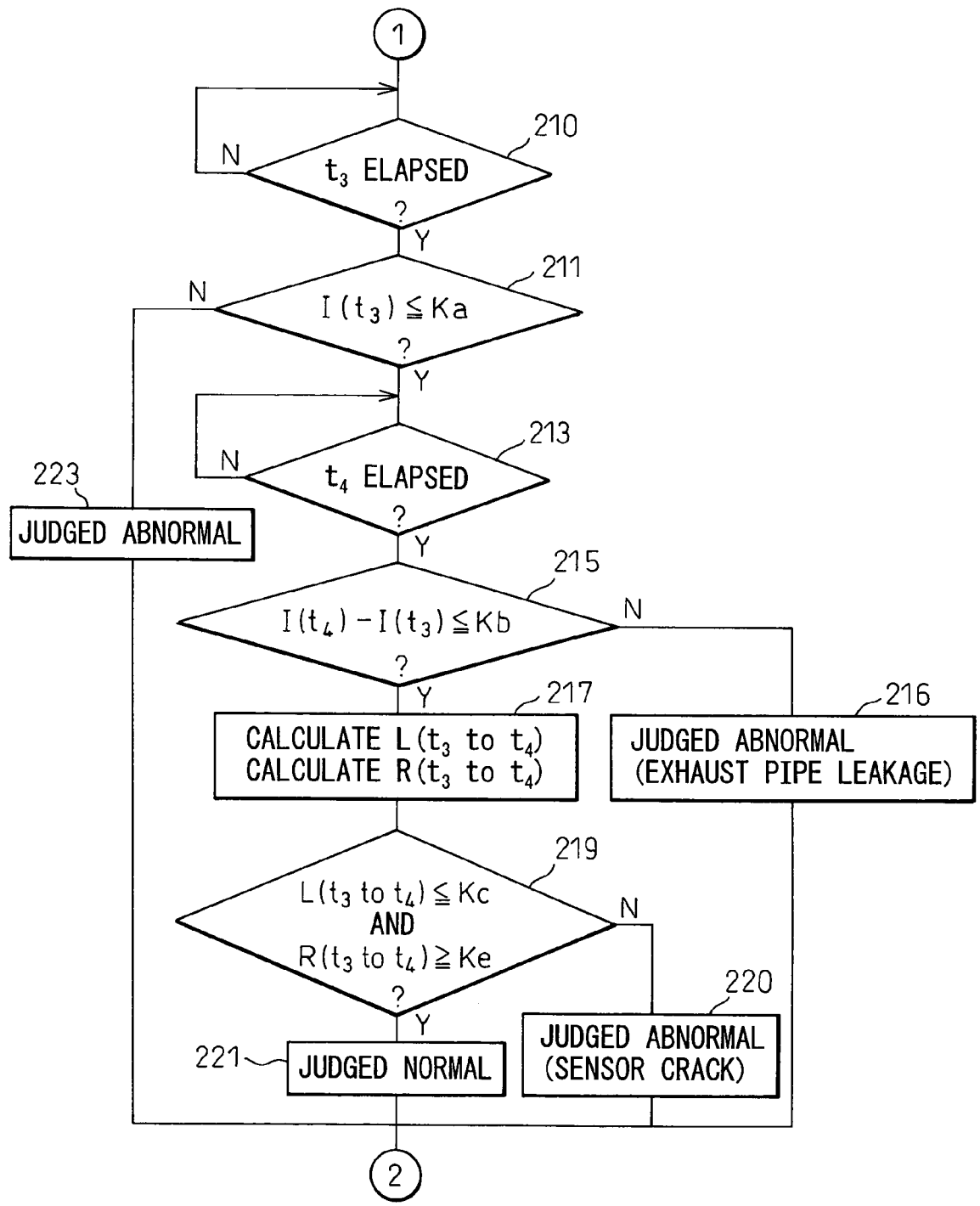
FIG. 10 is another control routine part able to be substituted for the control routine part shown in FIG. 6.

Further, in the process of judging if there is an abnormality by the control routine part shown in FIG. 6 of the above control routine, it is not yet judged if the cause of the abnormality occurring is leakage of the exhaust pipe or cracking of the sensor, but in another embodiment, it is also possible to replace the control routine part shown in FIG. 6 by the part shown in FIG. 10 to try to further judge the cause of the abnormality.

The process of judging if there is an abnormality by the control routine part shown in FIG. 10 basically performs the control from step 111 to step 121 after the elapse of the above third predetermined time t3. Due to this, the cause of the abnormality is judged in the same way as the above step 111 to step 121. More particularly, the steps from step 111 to step 121 in FIG. 5 correspond to the steps from step 211 to step 221 in FIG. 10. The gists and contents of the control at the different steps are believed to be clear from the explanation of the above step 111 to step 121, so a detailed explanation will be omitted here. Note that the t4 in the control routine part shown in FIG. 10 is the fourth predetermined time, which is the time elapsed after the internal combustion engine stops longer than the third predetermined time t3. Further, as clear from FIG. 10, even in this process of judging if there is an abnormality, sometimes the control is ended without judging the cause of the abnormality. That is, when the degree of the leanness of the air-fuel ratio of the exhaust gas remains high even when the third predetermined time t3 has elapsed at step 211 and it is judged that the output current I(t3) is larger than the predetermined value Ka, the routine proceeds to step 223, where it is only judged that there is an abnormality.

In the above embodiment, note that an abnormality of the air-fuel ratio sensor 10 was detected mainly based on the output of the air-fuel ratio sensor 10 upon and/or after the first predetermined time t1 elapses after the internal combustion engine is stopped, but it is similarly possible to detect an abnormality in the air-fuel ratio sensor 10 based on the speed of change of the output of the air-fuel ratio sensor 10. That is, as explained earlier, when the above air-fuel ratio sensor 10 is provided and is maintained in activity even after the internal combustion engine is stopped, the air-fuel ratio of the exhaust gas in the exhaust passage of the internal combustion engine will stabilize a little while after the internal combustion engine is stopped, then will gradually change to the stoichiometric air-fuel ratio by the reaction at the air-fuel ratio sensor 10. This change of the air-fuel ratio occurs due to the reaction at the air-fuel ratio sensor 10, so if an abnormality occurs in the air-fuel ratio sensor 10, the speed of change of the output of the air-fuel ratio sensor 10 (that is, the output current I) will be affected. For example, when the speed of reaction falls due to deterioration of the air-fuel ratio sensor 10, the speed of change of the output of the air-fuel ratio sensor 10 becomes smaller. Further, the degree of leakage of the exhaust pipe 6 etc. also affects the speed of change of the output of the air-fuel ratio sensor 10.

Due to this, if detecting the speed of change of output of the air-fuel ratio sensor 10, it is possible to accurately detect an abnormality of the air-fuel ratio sensor 10 based on this. Further, it is possible to estimate the extent of deterioration of the air-fuel ratio sensor 10, the extent of leakage of the exhaust pipe 6, etc. Note that detection of the speed of change of the output of the air-fuel ratio sensor 10 is possible by monitoring the output current I of the air-fuel ratio sensor 10.

While the invention has been described with reference to specific embodiments chosen for purpose of illustration, it should be apparent that numerous modifications could be made thereto by those skilled in the art without departing from the basic concept and scope of the invention.

What is claimed is:

1. An abnormality detection device for an air-fuel ratio sensor provided with:
   an air-fuel ratio sensor arranged in an exhaust passage of an internal combustion engine for detecting an air-fuel ratio based on a current generated in accordance with a concentration of oxygen in the exhaust gas along with application of voltage and
   an air-fuel ratio sensor activating means for activating said air-fuel ratio sensor, wherein
   the activity of said air-fuel ratio sensor is maintained even after the internal combustion engine is stopped and an abnormality of the air-fuel ratio sensor is detected based on an output of said air-fuel ratio sensor upon and/or after the elapse of a first predetermined time after the internal combustion engine is stopped.

2. An abnormality detection device for an air-fuel ratio sensor as set forth in claim 1, wherein it is judged that the output of said air-fuel ratio sensor is abnormal when a magnitude of the output of said air-fuel ratio sensor when said first predetermined time has elapsed is larger than a predetermined magnitude.

3. An abnormality detection device for an air-fuel ratio sensor as set forth in claim 1, wherein it is judged that said air-fuel ratio sensor has cracked when an amplitude of the output of said air-fuel ratio sensor after the elapse of said first predetermined time is larger than a predetermined amplitude.

4. An abnormality detection device for an air-fuel ratio sensor as set forth in claim 3, wherein judgment of cracking of said air-fuel ratio sensor is not performed when an air-fuel ratio shown by the output of said air-fuel ratio sensor when said first predetermined time has elapsed is leaner than a predetermined air-fuel ratio.

5. An abnormality detection device for an air-fuel ratio sensor as set forth in claim 1, wherein it is judged that there is a leak in an exhaust pipe forming said exhaust passage when the output of said air-fuel ratio sensor when a second predetermined time longer than said first predetermined has elapsed after the internal combustion engine has stopped changes to the lean side more than a predetermined change from the output of said air-fuel ratio sensor when said first predetermined time has elapsed.

6. An abnormality detection device for an air-fuel ratio sensor as set forth in claim 5, wherein judgment of leakage of the exhaust pipe is not performed when the air-fuel ratio shown by the output of the air-fuel ratio sensor when said first predetermined time has elapsed is leaner than a predetermined air-fuel ratio.

7. An abnormality detection device for an air-fuel ratio sensor as set forth in claim 4, wherein when the air-fuel ratio shown by the output of said air-fuel ratio sensor when said first predetermined time has elapsed is leaner than said predetermined air-fuel ratio, an abnormality of said air-fuel ratio sensor is detected based on the output of said air-fuel ratio sensor upon and/or after the elapse of a third predetermined time longer than said first predetermined time from when the internal combustion engine is stopped.

8. An abnormality detection device for an air-fuel ratio sensor as set forth in claim 6, wherein when the air-fuel ratio shown by the output of said air-fuel ratio sensor when said first predetermined time has elapsed is leaner than said predetermined air-fuel ratio, an abnormality of said air-fuel ratio sensor is detected based on the output of said air-fuel ratio sensor upon and/or after the elapse of a third predetermined time longer than said first predetermined time from when the internal combustion engine is stopped.

9. An abnormality detection device for an air-fuel ratio sensor provided with:
   an air-fuel ratio sensor arranged in an exhaust passage of an internal combustion engine for detecting an air-fuel ratio based on a current generated in accordance with a concentration of oxygen in the exhaust gas along with application of voltage and
   an air-fuel ratio sensor activating means for activating said air-fuel ratio sensor, wherein
   the activity of said air-fuel ratio sensor is maintained even after the internal combustion engine is stopped and an abnormality of the air-fuel ratio sensor is detected based on a speed of change of output of said air-fuel ratio sensor after the elapse of a first predetermined time after the internal combustion engine is stopped.

* * * * *